United States Patent [19]

Mizushima et al.

[11] Patent Number: 5,194,670

[45] Date of Patent: Mar. 16, 1993

[54] EMULSION OF LIPID CONTAINING A PROSTAGLANDIN ANALOGUE

[75] Inventor: Yutaka Mizushima, Tokyo; Toshihide Inomata, Tokyo; Arata Yasuda, Kanagawa; all of Japan

[73] Assignees: Yutaka Mizushima, Asahi Glass Company Ltd.; Seikagaku Corporation, Tokyo, Japan

[21] Appl. No.: 841,572

[22] Filed: Mar. 24, 1992

Related U.S. Application Data

[62] Division of Ser. No. 597,870, Oct. 12, 1990, Pat. No. 5,120,870.

[30] Foreign Application Priority Data

Oct. 16, 1989 [JP] Japan ................................. 1-266230

[51] Int. Cl.$^5$ ............................................. C07C 177/00
[52] U.S. Cl. ..................................................... 560/121
[58] Field of Search .......................................... 560/121

[56] References Cited

FOREIGN PATENT DOCUMENTS 0073397  3/1983  European Pat. Off. .
0097481  1/1984  European Pat. Off. .
0150732  8/1985  European Pat. Off. .

OTHER PUBLICATIONS

STN File Server & File Chemical Abstracts, vol. 105, No. 15, No. 128335s, A. K. Sim, et al., "The Effect of Prostaglandin E1 Incorporated in Lipid Microspheres on Thrombus Formation and Thrombus Disaggregation and its Potential to Target to the Site of Vascular Lesions", & Arzneim-Forsch, 36(8), 1206-9.

Primary Examiner—Paul J. Killos
Attorney, Agent, or Firm—Oblon, Spivak, McClelland, Maier & Neustadt

[57] ABSTRACT

An emulsion of lipid containing a prostaglandin analogue of the formula (1):

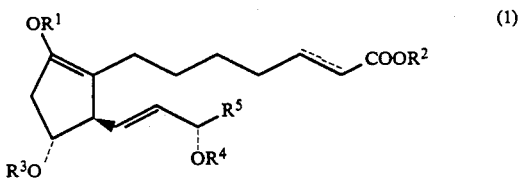

wherein $R^1$ is an alkanoyl group, $R^2$ is a hydrogen atom or an alkyl group, each of $R^3$ and $R^4$ is a hydrogen atom or a protective group for an alcohol, $R^5$ is an alkyl group which may have a substitutent, and ⎓ is a single bond or a double bond.

6 Claims, No Drawings

EMULSION OF LIPID CONTAINING A PROSTAGLANDIN ANALOGUE

This is a division of application Ser. No. 597,870, filed on Oct. 12, 1990, now U.S. Pat. No. 5,120,870.

The present invention relates to an emulsion of lipid containing a prostaglandin analogue and to specific prostaglandin analogues. For prostaglandins (hereinafter referred to as PG), six structures i.e. $PGE_1$, $PGE_2$, $PGE_3$, $PGF_{1\alpha}$, $PGF_{2\alpha}$ and $PGF_{3\alpha}$, were determined in 1960. Since then, PG analogues have been discovered one after another, and their physiological activities have been gradually known.

For example, methyl 9-acetoxy-11α, 15S-dihydroxy-prosta-8,13E-diene-1-oate of the formula (A), methyl 9,11α,15S-triacetoxyprosta-8,13E-diene-1-oate of the formula (B), methyl 9,15R-diacetoxy-11α-hydroxyprosta-8,13E-diene-1-oate of the formula (C) and 9,15S-diacetoxy-11α-hydroxyprosta-8,13-E-diene-1-oate of the formula (D) may be mentioned (U.S. Pat. No. 4,363,817).

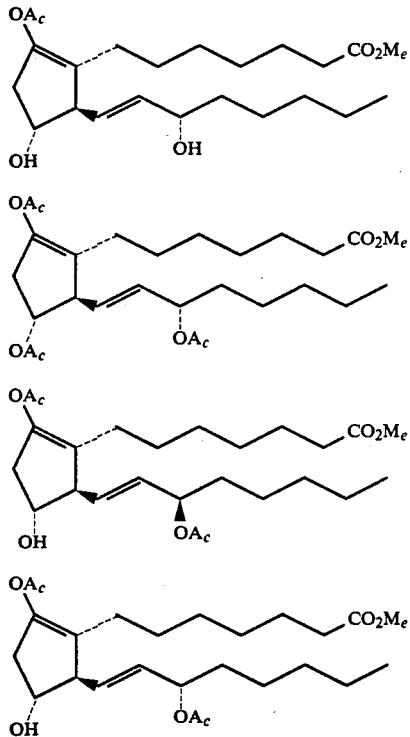

On the other hand, another literature predicts an important role which PGs will play as drugs in future and proposes that since PGs are typical local hormones which are produced locally as required and which act locally, it is necessary for such PG-related drugs to develop a drug delivery system taking into consideration the chemical properties and characteristics as autacoid. If a conventional general systemic administration method is employed, the effects are weak, and systemic side effects appear rather strongly. Therefore, it has been proposed to use lipid microspheres (hereinafter referred to as LM) as a carrier in the drug delivery system for PGs. However, such LM is believed to be emulsified fine particles of lipid containing PG.

Namely, it has been reported that the stability in vivo is increased by formulating $PGE_1$ into an emulsion of lipid containing $PGE_1$ as a target treating drug having $PGE_1$ encapsulated in LM having a diameter of 0.2 μm, and the formulated drug shows a vasodilator activity and platelet aggregation inhibiting activity stronger than $PGE_1$ alone (Sim, A.K., et al, Arznein-Forsch/-Drug Res., 1206-1209, 1986).

Further, it has been reported that when the $PGE_1$-containing lipid emulsion is administered to a vital body, a substantial amount of $PGE_1$ is freed from LM, and a study has been made to control the amount to be freed (Rie Igarashi et al, Ensho, 8, (3), 243-246 (1988)).

In the report, it is reported that with respect to the methyl ester, ethyl ester, butyl ester, pivalic acid ester and octyl ester of $PGE_1$, (1) the platelet aggregation inhibiting effect of each ester of $PGE_1$ was measured to study whether or not the activities would be obtained in vivo by the cleavage of the ester bond by an esterase even when the ester was per se inactive, and (2) the stability of each ester of $PGE_1$ as a LM drug was measured to study liberation of $PGE_1$ ester from LM by incubating it in a BSA-saline, to see the stability of the LM drug in blood (Tables 1(a) and 1(b) and Table 2).

TABLE 1

Inhibitory effects of $PGE_1$ and its esters against human platelet aggregation (a) Inhibitory effects against human platelet aggregation

|  |  | After incubating in human serum for 20 min |
|---|---|---|
| $PGE_1$ | 20.0 ± 3.3 ng/ml | 20.3 ± 4.3 ng/ml |
| $PGE_1$ methyl ester | 86.7 ± 14.7 ng/ml | 39.7 ± 11.3 ng/ml |
| $PGE_1$ ethyl ester | 101.0 ± 28.7 ng/ml | 72.3 ± 20.3 ng/ml |
| $PGE_1$ butyl ester | 68.0 ± 16.0 ng/ml | 22.7 ± 5.0 ng/ml |
| $PGE_1$ pivalyl ester | 192.0 ± 41.7 ng/ml | 34.3 ± 8.7 ng/ml |
| $PGE_1$ octyl ester | nd* | 431.7 ± 24.8 ng/ml |

(b) Inhibitory effects against human platelet aggregation

|  |  | After incubation in human serum for 20 min. |
|---|---|---|
| $PGE_1$ | 100 | 100 |
| $PGE_1$ methyl ester | 23 | 51 |
| $PGE_1$ ethyl ester | 20 | 28 |
| $PGE_1$ butyl ester | 29 | 89 |
| $PGE_1$ pivalyl ester | 10 | 59 |
| $PGE_1$ octyl ester | — | 4 |

*Not detectable as the activity is so low. (mean ± SE.n = 4-7)
Evaluated on the basis that the activity of $PGE_1$ is rated 100.

TABLE 2

Liberation of $PGE_1$ and its esters from the respective LM drugs when incubated in a 1.6% BSA-saline solution

| | % of $PGE_1$ (or ester) liberated from LM | |
|---|---|---|
| | 1 min incubation (5%) | 10 min incubation (%) |
| $PGE_1$ | 96.2 ± 2.1 | 90.7 ± 2.4 |
| $PGE_1$ methyl ester | 82.5 ± 3.8 | 80.4 ± 2.9 |
| $PGE_1$ ethyl ester | 82.0 ± 8.8 | 125.4 ± 11.7 |
| $PGE_1$ butyl ester | 60.5 ± 4.0 | 65.3 ± 5.6 |
| $PGE_1$ pivalyl ester | 51.6 ± 2.8 | 83.1 ± 5.1 |
| $PGE_1$ octyl ester | nd* | nd* |

*Not detectable as the activity is so low (mean ± SE.n = 4-7)

In order to improve the gradual releasability of $PGE_1$ esters, it is necessary to finely disperse $PGE_1$ ester-containing LM in water for the production of LM drugs. For this purpose, $PGE_1$ esters, lipids and other materials are required to be homogenized in water at a high temperature of from about 80° to 90° C., as will be described hereinafter. Under such a high temperature condition, conventional PGE₁ is likely to be rapidly decomposed.

Further, conventional PGE₁ is poor in the storage stability and is likely to undergo decomposition also in the course of distribution of the commercial products.

It is a first object of the present invention to develop PGE₁ analogues excellent in the stability even when formulated under a high temperature condition.

It is a second object of the present invention to develop an emulsion of a PGE₁ analogue having improved storage stability even in the course of distribution.

Namely, the present invention provides an emulsion of lipid containing a prostaglandin analogue of the formula (1):

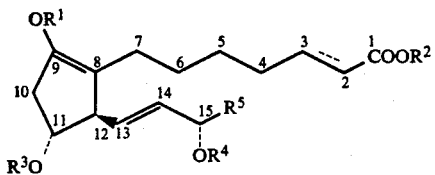

wherein $R^1$ is an alkanoyl group, $R^2$ is a hydrogen atom or an alkyl group, each of $R^3$ and $R^4$ is a hydrogen atom or a protective group for an alcohol, $R^5$ is an alkyl group which may have a substituent, and ⎯ is a single bond or a double bond.

The present invention also provides prostaglandin analogues of the formulas (2) and (3):

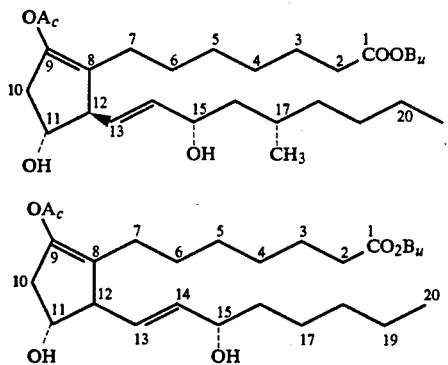

wherein Ac is an acetyl group, and Bu is a butyl group.

Now, the present invention will be described in detail with reference to the preferred embodiments.

In the prostaglandin analogue of the formula (1) of the present invention (hereinafter referred to as a PG analogue), $R^1$ may be an alkanoyl group having at most 6 carbon atoms such as acetyl, propionyl, iso propionyl or butyryl. It is preferably an alkanoyl group having at most 4 carbon atoms, more preferably an acetyl group.

$R^2$ may be a hydrogen atom or an alkyl group having from 1 to 6 carbon atoms.

The alkyl group may be methyl, ethyl, propyl, isopropyl, butyl or pentyl. Particularly preferred is a n-butyl group (hereinafter referred to simply as a butyl group).

Each of $R^3$ and $R^4$ is a hydrogen atom or a protective group for an alcohol. In compounds useful as medicines, each of $R^3$ and $R^4$ is usually a hydrogen atom.

The protective group for an alcohol may be an alkanoyl group of a lower alkyl group such as an acetyl group.

$R^5$ may be a substituted or unsubstituted alkyl group.

As such an alkyl group, a linear or branched alkyl group having from 3 to 8 carbon atoms may be mentioned. For example, it may be an alkyl group such as butyl, pentyl, hexyl, heptyl or octyl. Particularly preferred is a pentyl group or a 2-methylhexyl group.

The PG analogues of the present invention represented by the formulas (1), (2) and (3), have asymmetric carbon atoms at the 9-, 11-, 12- and 15-positions. Therefore, various steric isomers exist. The present invention may be applied to any one of such PG analogues and to a mixture thereof.

The PG analogues of the formulas (1), (2) and (3) of the present invention can be produced by a known process. For example, they may be produced by a process which comprises reacting a substituted 1-iodoalkene with an alkyl lithium to obtain a substituted 1 lithioalkene, then reacting it with a trialkylphosphine-copper (I) iodide complex to obtain an organolithiocuprate, and then reacting this organolithiocuprate with a substituted 2-cyclopenten-1-one by 1,4-conjugation addition, and then quenching the reaction mixture with a carboxylic anhydride, carboxylic mixed anhydrides or a carboxylic acid halide. The details of this process are disclosed in e.g. U.S. Pat. No. 4,363,817 or in literatures by Sih, et al. J. Am. Chem. Soc., 97,857,865 (1975), J. Am. Chem. Soc., 110, 3588 (1988).

In the present invention, the lipid preferably comprises from 5 to 50% (W/V) of a glyceride such as soybean oil, and phospholipid in an amount of from 1 to 50 parts, preferably from 5 to 30 parts, per 100 parts of the glyceride. Further, an emulsification-assisting agent (such as up to 0.3% (W/F) of a fatty acid having from 6 to 22 carbon atoms, preferably from 12 to 20 carbon atoms, or a physiologically acceptable salt thereof), a stabilizer (such as not more than 0.5% (W/V), preferably not more than 0.1% (W/V), of a cholesterol, or not more than 5% (W/V), preferably not more than 1% (W/V), of phosphatidic acid), a polymer substance (such as from 0.1 to 5 parts by weight, preferably from 0.5 to 1 part by weight, per part by weight of the PGE₁ analogue, of albumin, dextrane, a vinyl polymer, a non-ionic surfactant, gelatin, hydroxyethyl starch, etc.), or an isotonic agent (such as glycerol or glucose), may be added. The content of the PG analogue in the emulsion may suitably be adjusted depending upon the form and the purpose of the emulsion, and may usually be very small in the emulsion, for example, at a level of from 100 to 0.2 μg/ml.

Here, the soybean oil used as a glyceride is purified soybean oil having a high purity, preferably a highly pure purified soybean oil (purity: at least 99.9% as tri-glyceride, diglyceride and monoglyceride) obtained by further purifying the purified soybean oil by e.g. a steam distillation method.

The phospholipid is a purified phospholipid such as yolk lecitin or soybean lecitin, which may be prepared by a separation method by means of a usual organic solvent. Namely, for example, crude yolk phospholipid is dissolved in cool n-hexane/acetone, and acetone is gradually added under stirring, whereupon the insoluble component is recovered by filtration. This operation is repeated once more, followed by distillation of the solvent to obtain a purified phospholipid. This is composed mainly of phosphatidyl choline and phosphatidyl ethanolamine and may contain other phospholipids such as phosphatidyl inositol, phosphatidyl serine and sphingomyelin.

As an emulsification-assisting agent, any fatty acid having from 6 to 22 carbon atoms may be used, so long as it is acceptable as an additive to pharmaceuticals. This fatty acid may be linear or branched. However, it is preferred to employ linear stearic acid, oleic acid, linolic acid, palmitic acid, linoleic acid or myristic acid. As the salt thereof, a physiologically acceptable salt such as an alkali metal salt (sodium salt or potassium salt), or an alkaline earth metal salt (such as calcium salt) may be employed.

As the stabilizer, cholesterol or phosphatidic acid may be used so long as it is useful for pharmaceuticals.

As the albumin, the vinyl polymer and the nonionic surfactant to be used as the polymer substance, the following materials are preferred. Namely, as the albumin, the one derived from human is preferred in view of the question of the antigen nature.

As the vinyl polymer, polyvinylpyrrolidone may be mentioned.

Likewise, as the nonionic surfactant, a polyalkylene glycol (such as a polyethylene glycol having an average molecular weight of from 1000 to 10000, preferably from 4000 to 6000), a polyoxyalkylene copolymer (such as a polyoxyethylene-polyoxypropylene copolymer having an average molecular weight of from 1000 to 20000, preferably from 6000 to 10000), a hardened rapeseed oil polyoxyalkylene derivative (such as hardened rapeseed oil polyoxyethylene-(4)-ether, hardened rapeseed oil-(2)-ether, or hardened rapeseed oil-(100)-ether, or a rapeseed oil polyoxyalkylene derivative (such as rapeseed oil polyoxyethylene-(20)-ether, rapeseed oil polyoxyethylene-(40)-ether, or rapeseed oil polyoxyethylene-(100)-ether) may be employed.

The emulsion of the present invention may be produced by, for example, the following process.

Namely, predetermined amounts of soybean oil, lipid, a PG analogue and other additives as mentioned above, are mixed and heated to form a solution and subjected to homogenizing treatment by means of a usual homogenizer (such as a pressurized jet type homogenizer or an ultrasonic homogenizer) at a temperature of from about 80 to 90° C. to obtain a water-in-oil dispersion. Then, a necessary amount of water is added thereto, and the mixture is again homogenized by means of the above homogenizer to convert it into an oil-in-water type emulsion, whereby the emulsion of the present invention is prepared. Depending upon the convenience for the production, additives such as a stabilizer and an isotonic agent may be added after formation of the emulsion.

The emulsion of the present invention may be administered orally or non-orally. For example, in the case of intravenous administration, it is intravenously continuously injected once a day at a rate of from 0.22 to 2000 ng/kg/min at a dose of from 1 to 1000 μg/kg as the PG analogue.

Now, the present invention will be described in further detail with reference to Examples of the emulsions of the present invention and Preparation Examples of PG analogues. However, it should be understood that the present invention is by no means restricted to such specific Examples.

EXAMPLE 1

Preparation of butyl 9-actoxy-11α, 15S-dihyroxy-17S,20-dimethylprosta-8-13E-diene-1-oate (Formula (2))

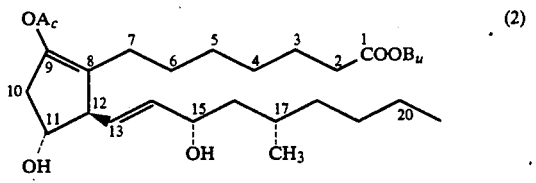

A solution of (1E,3S,5S)-1-iodo-3-(t-butyl dimethylsiloxy)-5-methyl-1-nonene (5.38 g, 13.56 mmol) in ethyl ether (100 ml) was cooled to $-78°$ C., and t-butyl lithium (f=1.5 hexane solution 18.1 ml, 27.1 mmol) was dropwise added thereto. The mixture was stirred at the same temperature for 2 hours, and then a solution of a tributylphosphine-copper(I) iodide complex (4.63 g, 12.31 mmol) and tributylphosphine (2.92 ml, 12.16 mmol) in ethyl ether (40 ml) was dropwise added thereto. The mixture was stirred at $-78°$ C. for 50 minutes, and then a solution of 4R-t-butyldimethylsiloxy-2-(6-carbobutoxyhexyl)-2-cyclopenten-1-one (4.75 ml, 11.3 mmol) in ethyl ether (160 ml) was dropwise added thereto. The mixture was stirred at $-78°$ C. for 20 minutes and further at from $-23°$ to $-18°$ C. for 35 minutes, and then acetic anhydride (3.0 ml, 30 mmol) was dropwise added thereto at 0° C., followed by stirring at from 0° C. to room temperature for 15 hours. Then, a saturated ammonium sulfate aqueous solution (200 ml) was added thereto. After separating from the organic layer, the aqueous layer was extracted twice with ethyl ether (100 ml), and the extract was combined to the organic layer. The combined organic layer was washed with a saturated sodium chloride aqueous solution (120 ml). The organic layer was dried over anhydrous magnesium and then filtered. The solvent was distilled off under reduced pressure. The residue was purified by silica gel chromatography (hexane/ethyl acetate=20/1 to 4/1) at 0° C. to obtain an adduct. The adduct thus obtained (5.5 g, 8.25 mmol) was dissolved in acetonitrile (100 ml), and a 40% hydrofluoric acid aqueous solution (10 ml) was added thereto at 0° C. The mixture was stirred at the same temperature for 30 minutes. The reaction solution was poured into a mixture of a 20% potassium carbonate aqueous solution (150 ml) and methylene chloride (150 ml). The mixture was dried over anhydrous magnesium sulfate and then filtered, and the solvent was distilled off under reduced pressure. The residue was purified by silica gel chromatography (methylene chloride/acetone=2/1) at 0° C. to obtain the above identified compound (3.27 g, yield: 83%).

$^1$H-NMR(CDCl$_3$): δ0.8–1.0(9H,m), 1.2–2.9 (30H,m+s(δ2.15,3H)), 3.1(1H,m), 4.05(2H,t,J=7Hz), 4.1–4.2(2H,m), 5.48(1H,dd,J=7Hz), 5.6(1H,dd,J=7Hz)

To 500 μg of the PG analogue of the formula (2) of the present invention produced as described above, 10 g of purified soybean oil and 1.2 g of purified yolk lecitin were added, and the mixture was melted under heating at 90° C. by means of a homogenizer at 90° C. Then, 2.5 g of glycerol and 90 ml of distilled water for injection were added thereto, followed by rough emulsification by means of a homogenizer at 90 μ. The product is then emulsified by means of a manton gaulin type homogenizer to obtain an emulsion having a final concentration of 5 μg/ml.

The stability of the PG analogue of the present invention during the preparation of the emulsion and the storage stability of the emulsion were measured, and the results are shown in Table 3.

EXAMPLE 2

Preparation of methyl 9-acetoxy-11α,15S-dihydroxyprosta-9,13E-diene-1-oate (Formula (4))

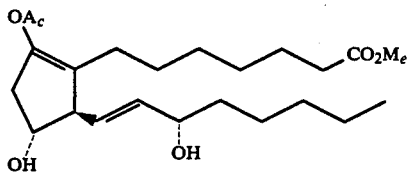

The above identified compound was prepared (yield: 66%) in the same manner as in Example 1 except that in the process described in Example 1, 4R-t-butyldimethylsiloxy-2-(6-carbomethoxyhexyl)-2-cyclopenten-1-one was used instead of (1E,3S,5S)-1-iodo-3-(t-butyldimethylsiloxy)-5-methyl-1-nonene.

$^1$H-NMR(CDCl$_3$): δ 0.9(3H,t,J=7Hz), 1.2 2.9 (25H,m+s(δ2.15,3H)),3.0–3.1(1H,m), 3.65(3H,s), 4.0–4.2(2H,m), 5.45(1H,dd,J=7.1Hz), 5.60(1H,dd,J=7Hz)

Then, the product was treated in the same manner as in Example 1 to obtain an emulsion of the present invention.

The stability of the PG analogue of the present invention during the preparation of the emulsion and the storage stability of the emulsion were measured, and the results are shown in Table 3.

EXAMPLE 3

Preparation of butyl 9-acetoxy-11α,15S-dihydroxyprosta-8,13E-diene-1-oate (Formula (3))

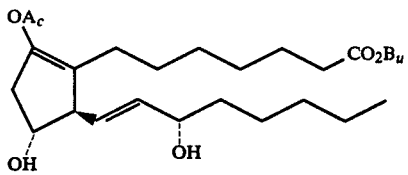

The above identified compound was prepared (340 mg, yield: 53%) in the same manner as in Example 1 except that in the process described in Example 1, (1E,3S)-1 iodo-3-(t-butyldimethylsiloxy)-1-octene (4.95 g, 13.44 was used instead of (1E,3S,5S)-1-iodo-3-(t-butyldimethylsiloxy)-5-methyl-1-nonene.

$^1$H-NMR(CDCl$_3$): δ0.85(3H,t,J=7Hz), 0.95(3H,t,J=7Hz), 1.2–2.9(29H,M+S(δ2.15,3H,s)), 3.0–3.05(1H,m), 4.1(2H,t,J=7Hz), 4.0–4.2(2H,m), 5.45(1H,dd,J=7Hz), 5.6(1H,dd,J=7.1Hz)

Then, the product was treated in the same manner as in Example 1 to obtain an emulsion of the present invention. The stability of the PG analogue of the present invention during the preparation of the emulsion and the storage stability of the emulsion were measured, and the results are shown in Table 3.

EXAMPLE 4

Preparation of methyl 9-acetoxy-11α,15S-dihydroxy-17S,20-dimethylprosta-8,13E-diene-1-oate (Formula (5))

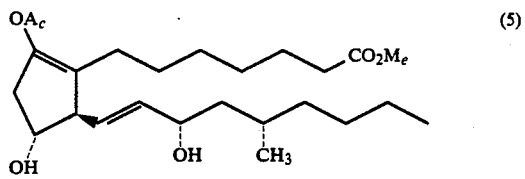

The above identified compound was prepared (yield: 72%) in the same manner as in Example 1 except that in the process described in Example 1, (1E,3S,5S)-1-iode 3-(t-butyldimethylsiloxy)-5-methyl-1-nonene was used instead of (1E,3S,5S)-1-iodo-3-(t-butyldimethylsiloxy)-5-methyl-1-nonene, and 4R-trimethylsiloxy-2-(6-carbomethoxyhexyl)-2-cyclopenten-1-one was used instead of 4R-t-butyldimethylsiloxy-2-(6-carbobutoxyhexyl)-2-cyclopenten-1-one.

$^1$H-NMR(CDCl$_3$):δ0.8–0.95(6H,m), 1.0–2.9 (21H,m+s(δ2.05,3H)), 3.05(1H,m), 3.65(3H,s), 4.0–4.2(2H,m), 5.45(1H,dd,J=7.1Hz), 5.6(1H,dd,J=7Hz)

Then, the product was treated in the same manner as in Example 1 to obtain an emulsion of the present invention.

The stability of the PG analogue of the present invention during the preparation of the emulsion and the storage stability of the emulsion were measured, and the results are shown in Table 3.

EXAMPLE 5

Preparation of butyl 9,11-diacetoxy-11α,15S-dihydroxyprosta-8,13E-diene-1-oate (Formula (6))

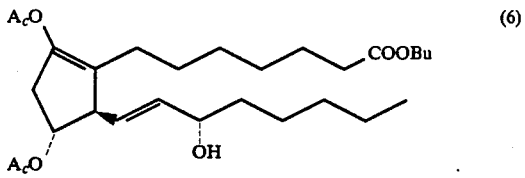

A solution of (1E,3S)-1-iodo-3-(t-butyldimethylsiloxy)-1-octene (1.27 g, 3.44 mmol) in ethyl ether (14.4 mmol) was cooled to −78° C., and t-butyl lithium (f=1.6 hexane solution 4.3 ml, 6.46 mmol) was dropwise added thereto. The mixture was stirred at the same temperature for 2 hours, and then a solution of a tributylphosphine-copper(I) iodide complex (1.18 g, 3.16 mmol) in ethyl ether (11.5 ml) was dropwise added thereto. The mixture was stirred at −78° C. for 50 minutes, and then a solution of 4R-trimethylsiloxy-2-(6-carbobutoxyhexyl)-2-cyclopenten-1-one (1.0 g, 2.87 mmol) in ethyl ether (45.8 ml) was dropwise added thereto. The mixture was stirred at −78° C. for 20 minutes and further at from −30° to −20° C. for 30 minutes, and then acetic anhydride (0.73 ml, 7.75 mmol) was dropwise added thereto at 0° C. The mixture was stirred at from 0° C. to room temperature for one hour. The reaction solution was poured into a saturated ammonium sulfate aqueous solution (100 ml). After separating the organic layer, the aqueous layer was extracted with ethyl ether (100 ml). The organic layers were put together and dried over anhydrous magnesium sulfate and then filtered. The solvent was distilled off under reduced pressure. The residue was purified by silica gel chromatography (hexane/ethyl acetate=40/1 to 10/1) at 0° C. to obtain an adduct. The adduct thus obtained (820 mg, 1.29 mmol) was dissolved in ethanol (6.6 ml), and p-toluenesulfonic acid pyridinium salt (32 mg, 0.13 mmol) was added at 0° C. The mixture was stirred at room temperature for one hour. The reaction solution was poured into a saturated sodium hydrogen carbonate aqueous solution, and extracted three times with methylene chloride (30 ml). The organic layers were put together and dried over anhydrous magnesium sulfate, and then filtered. The solvent was distilled off under reduced pressure. The residue was purified by silica gel chromatography (hexane/ethyl acetate=10/1 to 4/1) at 0° C. to obtain a 11-hydroxy product. This 11-hydroxy product (726 mg, 1.28 mmol) was dissolved in methylene chloride (8 ml), and pyridine (0.52 ml, 6.34 mmol), acetic anhydride (0.36 ml, 3.86 mmol) and 4-dimethylaminopyridine (1 mg) were added at 0° C. The mixture was stirred at room temperature for 4 hours. The reaction solution was poured into a mixture of a saturated sodium hydrogencarbonate (50 ml) and methylene chloride (20 ml). After separating the organic layer, the aqueous layer was extracted with methylene chloride (30 ml). The organic layers were put together and dried over anhydrous magnesium sulfate, and then filtered. The solvent was distilled off under reduced pressure. The residue was purified by silica gel chromatography (hexane/ethyl acetate=10/1) at 0° C. to obtain a 9,11-diacetoxy product. This diacetoxy product (706 mg, 1.10 mmol) was dissolved in acetonitrile (5 ml), and a 40% hydrofluoric acid aqueous solution (3.1 ml) was added at 0° C. The mixture was stirred at the same temperature for one hour. The reaction solution was poured into a mixture of a 20% potassium carbonate aqueous solution (150 ml) and methylene chloride (50 ml). The reaction solution was dried over anhydrous magnesium sulfate and then filtered, and the solvent was distilled off under reduced pressure. The residue was purified by silica gel chromatography (hexane/acetic acid = 10/1 to 1) at 0° C. to obtain the above identified compound (567 mg, yield: 41.6%).

$^{1}$H-NMR(CDCl$_3$): δ 0.86(3H,t,J=7.2Hz), 0.93(3H,t,J=7.2Hz), 1.2–1.9(22H,m), 2.28(1H,t,J=7.7Hz), 2.45(1H,m), 2.9–3.1(1H,m), 3.2–3.3(1H,m), 4.0–4.2(4H,m), 4.9 5.1(1H,m), 5.5–5.7(2H,m)

EXAMPLE 6

Preparation of butyl 9-butyroxy-11α,15S-dihydroxyprosta-8,13E-diene-1-oate (Formula (7))

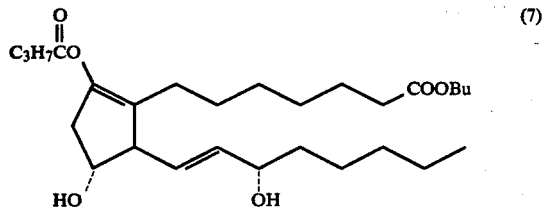

The above identified compound was obtained in a yield of 73.6% in the same manner as in Example 1 except that (1E,3S) 1-iodo-3-(t butyldimethylsiloxy) 1-octene was used instead of (1E,3S,5S)-1-iodo 3-(t-butyldimethylsiloxy)-5-methyl 1-nonene as the ω chain, and butyric anhydride was used instead of acetic anhydride.

1H-NMR(CDCl$_3$): δ 0.86–1.0(9H,m), 1.2–2.42(29H,m), 2.8–2.95(1H,m), 3.0–3.1(1H,m), 4.0–4.2(4H,m), 5.4–5.7(2H,m)

Table 3 shows the comparison in the stability during the preparation of the emulsion and the storage stability between various PG analogues prepared in the foregoing Examples. Further, for the purpose of comparison, similar treatments were conducted with respect to PGE$_1$, and the stability and the storage stability were compared in the same manner. The results are shown also in Table 3.

Further, the platelet aggregation inhibiting effects were measured as follows, and the results are shown also in Table 3.

Using sodium citrate (3.8%), peripheral blood was collected (blood 9, sodium citrate 1). This peripheral blood was subjected to centrifugal separation at 1000 rpm for 10 minutes to obtain a platelet rich plasma, and the rest was subjected to centrifugal separation at 3000 rpm for 20 minutes to obtain a plate poor plasma. To 225 μl of the platelet rich plasma, 50 μl of a test sample was added. One minute later, platelet aggregation was induced with 20 μMADP solution 25, whereupon the aggregation inhibitory rate (%) was calculated based on the aggregation rate when a physiological saline solution was added instead of the test sample, being rated as 100%.

TABLE 3

| | | Storage stability | | |
|---|---|---|---|---|
| Example No. | Stability during the preparation (%) | Remaining rate (%) | Decomposition reaction rate constant ($d^{-1} \times 10^3$) | Platelet aggregation inhibitory effects (%) |
| 1 | 75.6 | 84.8 | 6.20 | 37 |
| 2 | 70.4 | 72.7 | 11.8 | 100 |
| 3 | 72.1 | 80.1 | 8.30 | 93 |
| 4 | 68.3 | 77.9 | 8.87 | 44 |
| PGE$_1$ | 43.9 | 4.6 | 113 | 55 |

Storage stability: Stored for 4 weeks under a temperature condition of 40° C., and the remaining rate (%) after the 4 weeks was measured. Further, from the change with time of the remaining rate, the decomposition reaction rate constant was calculated.

The stability during the preparation and the remaining rate in the storage stability was measured by a separation quantitative analysis by means of high performance liquid chromatography, and the ratio of the measured amount relative to the amount at the initiation of the test was taken as the remaining rate. As compared with the emulsion of PGE$_1$, the emulsions of PG analogues of the present invention are all superior in the stability during the preparation and in the stability during the storage.

In addition to such effects, the emulsions of the PG analogues of the present invention are expected to be effective in the gradual releasing properties, focus selectivity, quick-acting properties and reduction of side effects.

We claim:

1. A prostaglandin analogue of the formula:

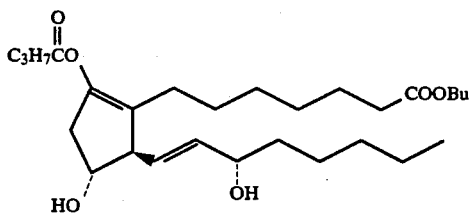

wherein Bu is a butyl group.

2. An emulsion of lipid containing a prostaglandin analogue of the formula:

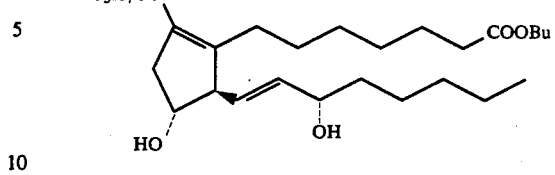

wherein Bu is a butyl group.

3. The emulsion according to claim 2, wherein the lipid is a lipid comprising a glyceride and a phospholipid as the main components.

4. The emulsion according to claim 2, wherein the amount of the prostaglandin analogue in the emulsion is from 0.2 to 100 μg/ml.

5. The emulsion according to claim 2, wherein said emulsion is an oil-in-water type emulsion.

6. The emulsion according to claim 2, wherein said emulsion is obtained by homogenizing a lipid containing the prostaglandin analogue in water at a temperature from 80° to 90° C.

* * * * *